(12) United States Patent
Chmielewski et al.

(10) Patent No.: US 6,699,228 B1
(45) Date of Patent: Mar. 2, 2004

(54) DIAPER FOR ISOLATING BOWEL MOVEMENT OR STOOLS FROM SKIN

(75) Inventors: Harry Joseph Chmielewski, Norcross, GA (US); Ebba A. Hansen, Lawrenceville, GA (US)

(73) Assignee: Paragon Trade Brands, Inc., Norcross, GA (US)

(*) Notice: Subject to any disclaimer, the term of this patent is extended or adjusted under 35 U.S.C. 154(b) by 0 days.

(21) Appl. No.: 09/095,879

(22) Filed: Jun. 11, 1998

(51) Int. Cl.[7] .................... A61F 13/15; A61F 13/20
(52) U.S. Cl. ................... 604/385.28; 604/385.19; 604/368; 604/374
(58) Field of Search ................... 604/347, 348, 604/385.01, 385.101, 385.19, 385.21, 385.23, 385.24, 385.3, 397, 398, 368, 374

(56) References Cited

U.S. PATENT DOCUMENTS

| | | | |
|---|---|---|---|
| 4,496,360 A | | 1/1985 | Joffe et al. ................ 604/397 |
| 4,573,990 A | * | 3/1986 | Ohsaki ................ 604/385.201 |
| 4,610,678 A | * | 9/1986 | Weisman et al. ........... 604/368 |
| 4,770,657 A | | 9/1988 | Ellis et al. |
| 5,405,342 A | * | 4/1995 | Roessler et al. |
| 5,516,569 A | * | 5/1996 | Verth et al. |
| 5,527,302 A | * | 6/1996 | Andres et al. |
| 5,669,896 A | * | 9/1997 | Kielpikowski ......... 604/385.28 |
| 5,716,350 A | * | 2/1998 | Ryan ..................... 604/394 |
| 5,716,351 A | * | 2/1998 | Roe et al. .............. 604/385.21 |
| 5,746,730 A | * | 5/1998 | Suzuki et al. .......... 604/385.26 |
| 5,766,411 A | | 6/1998 | Wilson .................. 156/495 |
| 5,779,690 A | * | 7/1998 | Gustafsson et al. |
| 5,853,403 A | * | 12/1998 | Tanzer et al. .......... 604/385.1 |
| 5,897,544 A | * | 4/1999 | Ronnberg ............... 604/385.2 |
| 2002/0068920 A1 | * | 6/2002 | Mishima ................ 604/385.28 |
| 2002/0099351 A1 | * | 7/2002 | Onishi et al. .......... 604/385.19 |
| 2002/0111594 A1 | * | 8/2002 | Onishi et. al. .......... 604/379 |
| 2002/0120248 A1 | * | 8/2002 | Onishi et al. .......... 604/385.19 |

FOREIGN PATENT DOCUMENTS

| | | | | |
|---|---|---|---|---|
| FR | 2701389 | * | 8/1994 | .............. 604/353 |
| JP | 8191857 A | * | 7/1996 | |
| JP | 8196565 A | * | 8/1996 | |
| WO | WO 9608225 A1 | * | 3/1996 | |

OTHER PUBLICATIONS

International Search Report–PCT/US99/13106.

\* cited by examiner

Primary Examiner—Karin Reichle
(74) Attorney, Agent, or Firm—Hunton & Williams

(57) ABSTRACT

A disposable absorbent garment includes a topsheet, a backsheet and an absorbent core disposed therebetween. A pair of inboard leg gathers are attached to the topsheet on opposite sides of a longitudinal centerline of the absorbent article and extend at least through the crotch area. The absorbent garment further includes an upper, partial length absorbent structure. The upper absorbent structure has a front edge extending near the front waist opening and a rear edge terminating in the area of the crotch region. A second pair of inboard leg gathers are positioned inboard of the first pair of leg gathers, and disposed on top of the upper absorbent structure. A BM containment pocket is formed beneath the upper absorbent structure. The BM containment pocket reduces mixing of urine and BM and prevents soiling of genitals, thereby reducing the incidence and severity of diaper rash.

21 Claims, 8 Drawing Sheets

DIAPER FOR ISOLATING BOWEL MOVEMENT OR STOOLS FROM SKIN

FIELD OF THE INVENTION

The present invention relates generally to disposable absorbent garments and more particularly to disposable absorbent products having improved bowel movement (BM) containment means including a pocket for containing and isolating BM to prevent the soiling of genitals.

BACKGROUND OF THE INVENTION

Traditionally, disposable absorbent garments such as infant diapers or training pants, adult incontinence products and other such products are constructed with a liquid-impervious outer backing sheet, a liquid-pervious body-contacting inner liner sheet, and a liquid-absorbent core sandwiched between the liner and backing sheets.

Some of the major challenges facing diaper manufacturers include the containment of BM and urine long enough so that it may be absorbed into the absorbent core. Subsequent insults, which typically take longer to be absorbed due to a partially saturated absorbent core, have been particularly troublesome. Inboard leg gathers contain and trap laterally flowing BM and urine, allowing more time to absorb the waste products.

Diaper rash can occur when absorbent articles do not adequately breathe, i.e., allowing the passage of air between and through the article to the wearer's skin. Since the backsheet is commonly liquid impermeable, its ability to pass air is typically diminished. In response, a number of manufacturers now provide disposable absorbent articles which, though containing liquid impermeable backing materials, nevertheless pass air through the article to improve comfort. Consequently, this contributor to diaper rash has been largely addressed with the introduction of state of the art materials in absorbent articles.

However, another significant contributor to diaper rash extends beyond the "breathability" of the absorbent article. This contributor is the result of the intermixing of urine and BM, which promotes microbial and enzymatic activity that can be harmful to skin. Incomplete removal of urine and BM between diaper changes promotes skin irritation and diaper rash, especially in the area of the genitals which are more difficult to clean. Breathable fibers and films do not solve this component. Thus, despite efforts to employ state of the art nonwovens and films to reduce the incidence of diaper rash, it continues to be problematic until urine and stool are isolated from one another and prevented from soiling genitals.

Proposals for depositing urine and stool into compartments have been disclosed for example in Williams, U.S. Pat. No. 4,662,877. Williams discloses an absorbent garment comprising an apertured topsheet, an absorbent core positioned beneath the apertured topsheet and sandwiched between a lower topsheet and a backsheet. The waste components are directed through the apertured topsheet into the lower compartment. The Williams apertured topsheet does not separate urine and stool. Rather, the urine is transported to the absorbent core through the lower compartment, which is precisely where the stool is located. As a consequence, urine and stool may intermingle.

Other proposals for containing stool within separate compartments of an absorbent garment have been made. For example, U.S. Pat. No. 5,558,660 to Dreier, discloses an absorbent article having a pocket cuff formed at a back end thereof and above the absorbent core. The Dreier pocket cuff functions as an end cap preventing the longitudinal migration of stool over the back waist portion of the diaper. Though disclosing an end cap for containing the longitudinal flow of stool, Dreier does not contemplate having absorbent material within the end cap. Further, the Dreier end cap does not prevent the forward migration of BM. In the event that the stool migrates forwardly in the Dreier absorbent article, it will have an opportunity to intermix with urine as well as soil the genitals. Thus, end caps such as disclosed by Dreier are generally not effective in isolating urine from BM, and not effective in preventing soiling of genitals.

These are but a few of the shortcomings and disadvantages of the prior art that the preferred embodiments seek to address.

SUMMARY OF THE INVENTION

It is an object of the preferred embodiments to provide a disposable absorbent garment which generally reduces the incidence of diaper rash.

It is another object of the preferred embodiments to provide a disposable absorbent garment which prevents the soiling of genitals after a bowel movement.

It is another object of the preferred embodiments to provide a disposable absorbent garment which prevents the soiling of genitals by collecting the bowel movement in a pocket formed in the diaper and isolating the collected BM from urine.

It is a further object of the preferred embodiments to prevent the soiling of genitals after a bowel movement by preventing the forward migration of BM in the direction of the genitals.

It is yet a further object of the preferred embodiments to provide a disposable absorbent garment incorporating a waste containment pocket into which stool may be directed without intermingling with urine.

It is still further yet another object of the preferred embodiments to provide an absorbent garment having a lower absorbent structure for the absorption and containment of stool, and an upper absorbent structure above the lower absorbent structure for absorbing and containing urine independently of the lower absorbent structure.

In another aspect of the invention, the upper and lower topsheets are formed from a continuous roll good material during manufacturing.

It is still yet a further object of the preferred embodiments to provide an absorbent garment having upper and lower absorption structures, wherein the lower absorption structure contains the main absorption core and the upper absorbent structure contains a secondary absorption core.

It is still yet a further object of the preferred embodiments to provide an absorbent structure which has two pairs of inboard or standing waste containment pockets or gathers, wherein the inner pair of standing gathers is associated with the upper absorbent structure and tends to encourage an open end of the upper absorbent structure to form an arched shaped opening into which BM may be collected, isolated and retained.

These and other objects of the preferred embodiments are achieved by an absorbent article having a front waist region, a rear waist region and a crotch region positioned between the front and rear waist regions. Leg elastics are optionally provided along the leg openings for securely holding the leg openings against the thighs of the wearer to improve containment and fit. A fastening system, either resealable or permanent, holds the absorbent article around the wearer's waist. A pair of stand-up leg gathers or waste containment flaps may be attached to or formed from the topsheet, and preferably extend from the front waist region to the rear waist region along opposite sides of a longitudinal centerline of the absorbent garment.

The absorbent core structure of the preferred embodiments includes a lower absorbent structure extending substantially from the front waist region to the rear waist region, and an upper absorbent structure extending from the front waist region to the crotch region. Alternatively, the lower absorbent structure preferably extends to a position in the crotch region subjacent a rear edge of the upper absorbent structure. The lower absorbent structure includes a lower absorbent core which is disposed between a lower topsheet and the backsheet, and may include other layers, including tissue and airlaid fluff pulp.

The upper absorbent structure includes an absorbent core (called the upper absorbent core) which is preferably similarly encased by a topsheet (upper topsheet) and optionally a backsheet and may include other intermediate transfer and acquisition layers including synthetic nonwoven, airlaid fluff pulp roll good and tissue. The upper absorbent structure is attached along three peripheral sides to the structure thereebeneath. More specifically, the front edge of the upper absorbent structure is generally attached near the front waist section, and the side edges of the upper absorbent structure are generally attached to the lower topsheet or backsheet at a point generally above the lateral side edges of the bottom absorbent core. The rear edge of the upper absorbent structure, on the other hand, is substantially unattached to the lower topsheet or other structure therebeneath. except at its corners.

Optionally, a second or inner pair of inboard waste containment flaps are positioned at the lateral side edges of the upper absorbent structure. The inner pair of waste containment flaps are, like the outer pair of waste containment flaps, elasticized at distal ends thereof. The elastics tend to contract when the tensile forces are removed. The contraction of the inner pair of waste containment flaps tends to encourage the rear edge of the upper absorbent structure to rise above the lower topsheet, forming an arched-shaped pocket opening. The pocket opening forms an entrance to a waste containment pocket formed between the upper absorbent structure and the components of the absorbent garment therebeneath.

During manufacturing, the lower absorbent structure preferably has a curved contour about the longitudinal axis imparted thereto at the time that the corners at the rear edge of the upper absorbent structure are secured to the lower topsheet. The curvature imparted to the lower absorbent structure tends to facilitate the opening of the arch-shaped waste containment pocket. The curvature on the lower absorbent structure predisposes the upper and lower absorbent structures to separate from one another even in the absence of elastics at the distal end of the inner pair of waste containment flaps.

The rear edge of the upper absorbent structure preferably extends at least partially into the crotch area so that when a wearer urinates, the urine tends to be contained by and within the upper absorbent core. Likewise, the upper absorbent structure is preferably sized so that when a wearer has a bowel movement, substantially all of the BM initially contacts the lower topsheet and tends to migrate in the direction of and into the waste containment pocket. Consequently, the absorbent garment of the preferred embodiments advantageously isolates urine and BM, prevents BM/urine from spreading and soiling genitals, and eliminates one of the significant contributors to diaper rash.

Further objects, features and advantages of the preferred embodiments of the invention will be further appreciated when the detailed description of the preferred embodiments is read in conjunction with the attached drawing figures.

DETAILED DESCRIPTION OF THE PREFERRED EMBODIMENTS

The preferred embodiments of the invention are directed to an improved absorbent garment having an upper and lower absorbent structure. The lower absorbent structure preferably extends substantially from the front waist region to the rear waist region, and the upper absorbent structure preferably extends from the front waist region to the crotch region. The upper absorbent structure is preferably attached along three peripheral edges to the lower absorbent structure. The rear edge of the upper absorbent structure corresponding to the crotch region is substantially directly unattached to the lower topsheet or surface of the lower absorbent structure. A curvature is generally imparted to the lower absorbent structure during manufacture such that when the absorbent garment is worn, a containment pocket is formed beneath the upper absorbent structure and between the upper and lower absorbent structures. The containment pocket includes a pocket opening defined beneath the rear edge of the upper absorbent structure. The pocket opening is adapted to collect solid waste for storage beneath the upper absorbent structure. The pocket opening thus isolates urine from BM and tends to prevent forwardly migrating BM from soiling the genitals.

As used herein, the term "absorbent garment" refers to garments that absorb and contain exudates, and more specifically, refers to garments which are placed against or in proximity to the body of the wearer to absorb and contain the various exudates discharged from the body. A non-exhaustive list of examples of absorbent garments includes diapers. diaper covers, disposable diapers, training pants, adult incontinence products and fern care products. The term "disposable absorbent garment" refers to absorbent garments that are intended to be discarded or partially discarded after a single use (i.e., they are not intended to be laundered or otherwise restored or reused). The term "unitary disposable absorbent garment" refers to a disposable absorbent garment that is essentially a single structure (i.e., it does not require separate manipulative parts such as a diaper cover and insert). As used herein, the term "diaper" refers to an absorbent garment generally worn by infants and incontinent persons about the lower torso.

The claims are intended to cover all of the foregoing classes of absorbent garments, without limitation, whether disposable, unitary or otherwise. These classifications are used interchangeably throughout the specification, but are not intended to limit the claimed invention. The invention will be understood to encompass, without limitation, all classes of absorbent garments, including those described above. Preferably, the absorbent core is thin in order to improve the comfort and appearance of the garment. The importance of thin, comfortable garments is disclosed, for example, in U.S. Pat. No. 5,098,423 to Pieniak et al., which is herein incorporated by reference.

Figure 1:
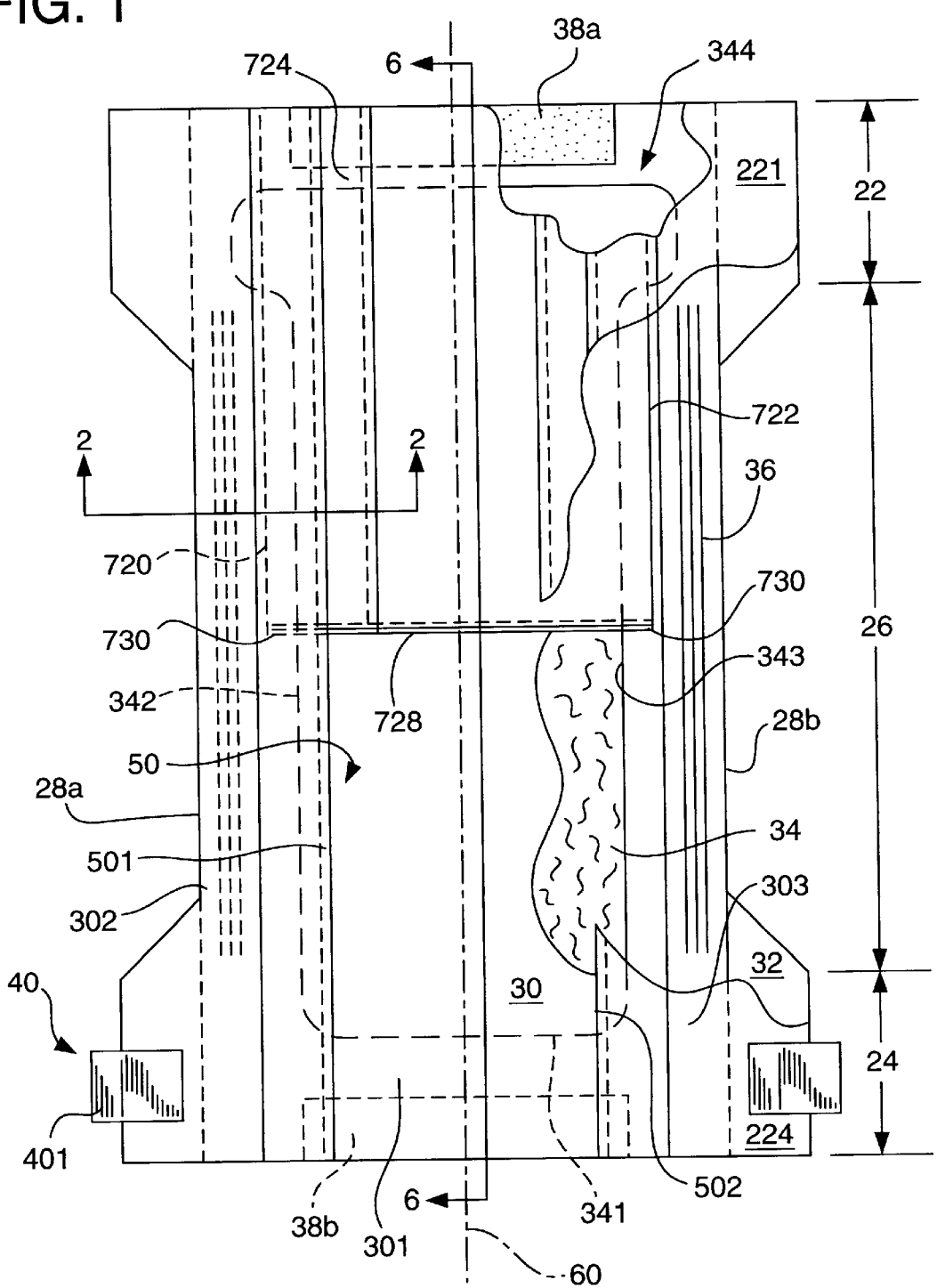
FIG. 1 is a partial cut away plan view of the absorbent garment according to the first preferred embodiment with the effects of the elastics removed.

A preferred embodiment of the present invention comprises a disposable absorbent garment 10 such as shown, for example, in FIG. 1. Again, it should be understood, however, that the present invention is applicable to other types of absorbent garments. For simplicity, the invention will be described in terms of a diaper. With reference to FIG. 1, the diaper 10 according to a first preferred embodiment is shown in a relaxed condition with the effects of the elastics removed for purposes of clarity in description. The diaper 10 has a generally hourglass shape and can generally be defined in terms of a front waist region 22, a back or rear waist region 24, and a crotch region 26. Alternatively, the diaper can be configured in a generally rectangular shape or in a T-shape. A pair of leg openings 28a, 28b extend along at least a portion of the crotch region 26. The diaper preferably comprises a lower topsheet 30, a backsheet 32, which may optionally be substantially co-terminous with the lower topsheet 30, and an absorbent core 34 disposed between at least a portion of the lower topsheet 30 and backsheet 32. One or more pairs of leg elastics 36 (three pairs are shown in FIG. 1) may optionally extend adjacent to leg openings 28a, 28b, respectively.

The diaper further may optionally include a front waist elastic system 38a, a back waist elastic system 38b, a fastening system 40 (e.g., tape or other suitable mechanical fastener) and a waste containment system 50 in the form of inboard leg gathers or waste containment flaps 501, 502. Inboard leg gathers 501, 502 (FIG. 2) preferably extend from the front waist region 22 to the back waist region 24 along opposite sides of a longitudinal center line or axial center line 60 of the diaper 10, or alternatively only along a portion thereof. The front waist region 22 and rear waist region 24 include ear portions 221, 224 extending outwardly from the leg openings 28a, 28b.

Due to the wide variety of backing and liner sheet construction and materials currently available, the invention is not intended to be limited to any specific materials or constructions of these components. The backsheet 32 is of any suitable pliable liquid-impervious material known in the art. Typical backsheet materials include films of polyethylene, polypropylene, polyester, nylon, and polyvinyl chloride and blends of these materials. For example, the backsheet can be of a pigmented polyethylene film having a thickness in the range of 0.02–0.04 mm. The moisture-pervious lower topsheet 30 can be of any suitable relatively liquid-pervious material known in the art that permits passage of liquid therethrough. Non-woven liner sheet materials are exemplary because such materials readily allow the passage of liquids to the underlying absorbent core 34. Examples of suitable liner sheet materials include non-woven webs of nylon, polyester and polypropylene fibers and blends of these materials.

The backsheet 32 and the lower topsheet 30 are "associated" with one another. The term "associated" encompasses configurations whereby the lower topsheet 30 is directly joined to the backsheet 32 by affixing the lower topsheet 30 directly to the backsheet 32, and configurations whereby the lower topsheet 30 is indirectly joined to the backsheet 32 by affixing the lower topsheet 30 through intermediate members, e.g., acquisition, transfer and/or tissue layers, which in turn are affixed to the backsheet 32. While the backsheet 32 and lower topsheet 30 in the preferred embodiment have substantially the same dimensions, they may also have different dimensions.

In addition, the backsheet 32 may be covered with a fibrous, nonwoven fabric such as is disclosed for example in U.S. Pat. No. 4,646,362, which is hereby incorporated by reference. Materials for such a fibrous outer liner include a spun-bonded nonwoven web of synthetic fibers such as polypropylene, polyethylene or polyester fibers; a nonwoven web of cellulosic fibers, textile fibers such as rayon fibers, cotton and the like, or a blend of cellulosic and textile fibers; a spun-bonded nonwoven web of synthetic fibers such as polypropylene; polyethylene or polyester fibers mixed with cellulosic, pulp fibers, or textile fibers; or melt blown thermoplastic fibers, such as macro fibers or micro fibers of polypropylene, polyethylene, polyester or other thermoplastic materials or mixtures of such thermoplastic macro fibers or micro fibers with cellulosic, pulp or textile fibers. Alternatively, the polypropylene or polyethylene backsheet may be positioned just beneath the core, with nonwoven fibrous outboard segments attached to either side of the rectangularly shaped poly backsheet. Still further yet, the poly backsheet may be made from a microporous material for added breathability either in the outboard segments of the backsheet, or across the entire width of the backsheet, including the central backsheet panel.

The lower topsheet 30 is preferably formed of three separate portions or panels. The first lower topsheet panel 301 may comprise a central topsheet panel formed from preferably a liquid-pervious material that is either hydrophobic or hydrophilic. The lower central topsheet panel 301 may be made from any number of materials, including synthetic fibers (e.g., polyester or polypropylene fibers), natural fibers (e.g., wood or cellulose), apertured plastic films, reticulated foams and porous foams to name a few. One preferred material for a lower central topsheet panel 301 is a cover stock of single ply non-woven material which may be made of carded fibers, either adhesively or thermally bonded, perforated plastic film, spunbonded fibers, or water entangled fibers, which generally weigh from 0.3–0.7 oz./sq. yd. and have appropriate and effective machine direction and cross-machine direction strength suitable for use as a baby diaper cover stock material. The lower central topsheet 301 panel preferably extends from substantially the front waist region 22 to the back waist region 24 or a portion thereof.

The second and third topsheet panels 302, 303 in this embodiment may be positioned laterally outside of the lower central topsheet panel 301. The outer topsheet panels 302, 303 are preferably substantially liquid-impervious and hydrophobic, preferably at least in the crotch area. The outer edges of the outer topsheet panels may substantially follow the corresponding outer perimeter of the backsheet 32. The material for the outer topsheet portions or panels is preferably polypropylene and can be woven, non-woven, spunbonded, carded or the like, depending on the application.

The inner edges 304 (FIG. 2) of the outer topsheet portions or panels 302, 303 preferably are attached by, e.g., an adhesive, to the outer edges 305 of the lower central topsheet portion or panel 301. At the point of connection with the outer edges 305 of the lower central topsheet portion or panel 301, the inner edges 304 of the outer topsheet portions or panels 302. 303 extend upwardly to form inboard leg gathers 501, 502. The inboard leg gathers 501, 502 are preferably formed of the same material as the outer topsheet portions or panels 302, 303, as in the embodiment shown. The inboard leg gathers 501, 502 are preferably an extension of the outer topsheet portions or panels 302, 303.

The inboard leg gathers 501, 502 may be treated with a suitable surfactant to modify their hydrophobicity/hydrophilicity as desired. Alternatively, the inboard leg gathers 501, 502 may be formed as separate elements and then attached to the lower topsheet panels 301. In this alternative embodiment, the lower central topsheet portion or panel 301 may extend past the connection point with the inboard leg gathers 501, 502, and even extend to the periphery of the backsheet. Still further, the lower central topsheet portion or panel 301 could extend fully between the outer topsheet portions or panels 302, 303 and even beyond so that the outer edges 305 of the lower central topsheet portion or panel 301 are coextensive with and sandwiched between the outer topsheet portions or panels 302, 303 and the backsheet 32.

The inboard leg gathers 501, 502 preferably include a portion 503 which folds over onto itself to form a small enclosure. At least one, and depending on the size of the enclosure sometimes more than one, elastic member 504 (FIG. 2) is secured in the enclosure in a stretched condition. As has been known at least as long the disclosure of Tetsujiro, Japanese Patent document 40-11543, when the flap elastic 504 attempts to assume the relaxed, unstretched condition, the inboard leg gathers 501, 502 rise above the surface of the lower central topsheet portion or panel 301. Alternatively, any other elasticizing means other than elastic member 504 may be used to elasticize inboard leg gathers 501, 502. Furthermore, due to the wide variety of constructions and materials currently available for inboard leg gathers, the invention is not intended to be limited to any specific materials or constructions of these components.

For example, the inboard leg gathers 501, 502 may be replaced with a unitary leg cuff such as is disclosed in commonly assigned U.S. patent application Ser. No. 08/853, 761 entitled Disposable Absorbent Article with Unitary Leg Gathers, filed on May 9, 1997. The unitary cuff of the alternative embodiment advantageously combines the inboard leg gathers and leg elastic containment system 36 into a unitary structure. In one such configuration, the unitary leg cuff has a proximal end attached to the topsheet and an unattached distal end. A plurality of spaced elastics are contained within the unitary leg cuff between the proximal end and the distal end. The elastic characteristics of the unitary leg cuff are selected so that the dual function of leg elastication as well as providing a barrier to the lateral flow of waste material may be provided in a single standing unitary leg cuff.

The waist elastics 38a, 38b may be similar structures or different to impart similar or different elastic characteristics to the front and back waist portions 22, 24 of the diaper. In general, the waist elastics 38a, 38b may comprise foam strips positioned at the front and back waist sections 22, 24. The foam strips are preferably about ½ to 1½ inches wide and about 3–6 inches long. The foam strips are preferably positioned between the topsheet portions or panels and the backsheet 32. Alternatively, waist elastics 38a, 38b may comprise a plurality of transversely extending elastic strands. The foam strips are preferably polyurethane, but could be any other suitable material which decreases waist band roll over, reduces leakage over the waist ends of the absorbent garment, and generally improve comfort and fit. The front and back waist foam strips 38a, 38b are stretched 50–150%, preferably 100% before being adhesively secured between the backsheet 32 and topsheet 30.

In any or all of the foregoing embodiments, the lower topsheet 30 may comprise a single sheet of material having different characteristics (e.g., liquid-imperviousness/perviousness and/or hydrophobicity/hydrophilicity) and have regions of transition or demarcation therebetween.

Optionally, each leg opening 28a, 28b is provided with a leg elastic 36 containment system. Due to the wide variety of leg elastic containment systems, constructions and materials currently available, the invention is not intended to be limited to any specific leg elastic containment constructions, system, or materials. In the preferred embodiment, three strands of elastic threads are positioned to extend adjacent to leg openings 28a, 28b between the outer topsheet portions or panels 302, 303 and the backsheet 32. Any suitable elastomeric material exhibiting at least an elongation (defined herein as $L_s$–$L_R$/$L_R$ where $L_s$ is the stretch length of an elastic element and $L_R$ is retracted length, multiplied by 100 to obtain percent elongation) in the range of 5%–350%, preferably in the range of 200%–300%, can be employed for the leg elastics 36. The leg elastics 36 may be attached to the diaper 10 in any of several ways which are known in the art. For example, the leg elastics 36 may be ultrasonically bonded, heat/pressure sealed using a variety of bonding patterns, or glued to the diaper 10.

Various commercially available materials can be used for the leg elastics 36, such as natural rubber, butyl rubber or other synthetic rubber, urethane, elastomeric materials such as that available from DuPont under the trademark LYCRA and elastomeric material available from Fulflex under the trademark SYSTEM 7000.

The fastening system 40 of the preferred embodiment is attached to the back waist region 24, and preferably comprises tape tab or mechanical fasteners 401. However, any fastening known in the art will be acceptable. Moreover, the fastening system 40 may include a reinforcement patch below the front waist portion so that the diaper may be checked for soiling without compromising the ability to reuse the fastener. Alternatively, other diaper fastening systems are also possible, including safety pins, buttons, and snaps.

The absorbent structure of the first preferred embodiment comprises a lower absorbent core 34 generally disposed between the lower central topsheet portion or panel 301 and the backsheet 32. The lower absorbent core 34 is generally defined by a rear edge portion 341 (FIG. 1) which extends in the direction of and terminates near the rear waist elastic 38b. The lower absorbent core 34 further is defined by side edges 342, 343 which are preferably disposed between the proximal edge (i.e., the edge of attachment) of the inboard leg gathers 501, 502. The lower absorbent core 34 is further defined by a front edge 344 which, in one preferred embodiment, extends to and terminates in the general vicinity of the front waist elastic 38a. In an alternative embodiment, the lower absorbent core 34 has a rear edge 341 disposed near the rear waist elastic and a front edge 344 extending to and terminating in the general vicinity of the middle of the crotch area 26.

The lower absorbent core 34 of the first preferred embodiment is preferably an airlaid fluff pulp roll good which may be impregnated with super absorbent polymer gelling particles. The airlaid fluff pulp basis weight, without SAP, is preferably in the range of about 30–150 grams per square meter, and most preferably about 60–120 grams per square meter. The lower absorbent core 34 preferably contains by weight about 10–60% SAP, and most preferably about 30–40% SAP. Alternatively, the lower absorbent core of the first preferred embodiment may comprise a multiplicity of tissue layers and/or synthetic nonwoven and/or airlaid fluff pulp layers. Tissue basis weights of about 10–40 grams per square meter and synthetic nonwoven basis weights of about 10–100 grams per square meter are preferred.

Figure 2:
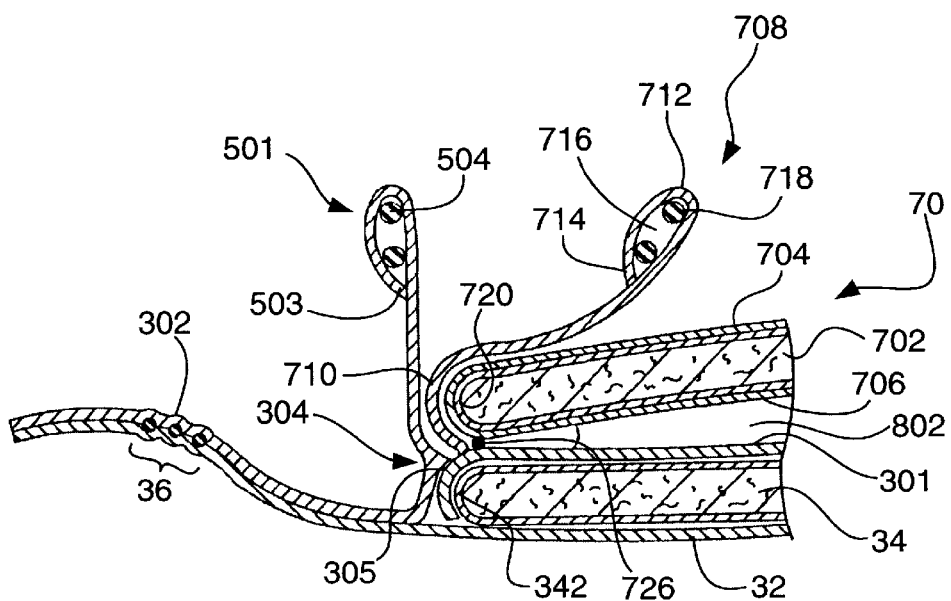
FIG. 2 is a partial cross-sectional view taken along line 2—2 in FIG. 1 showing the waste containment pocket opening.
Figure 3:
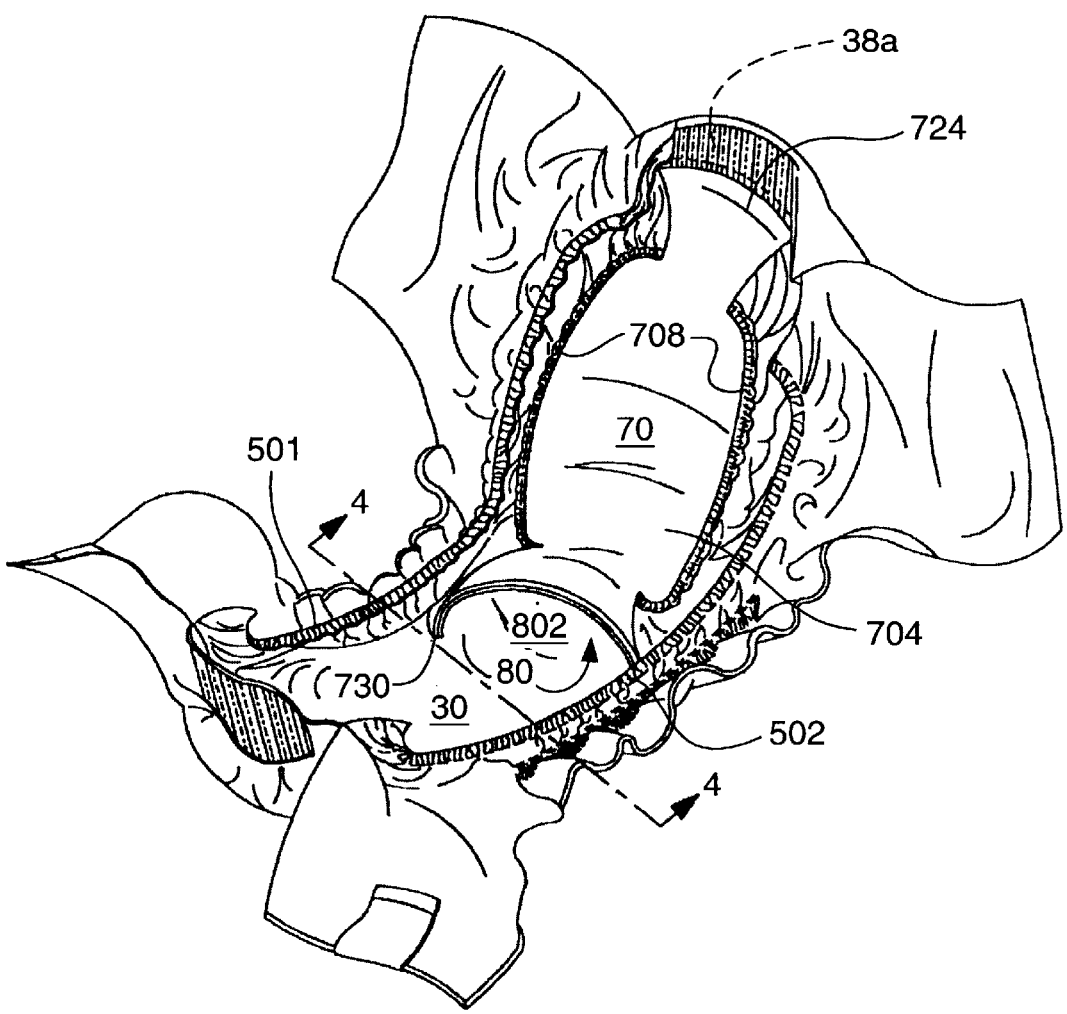
FIG. 3 is a perspective view of the absorbent garment according to the first preferred embodiment of the invention.
Figure 4:
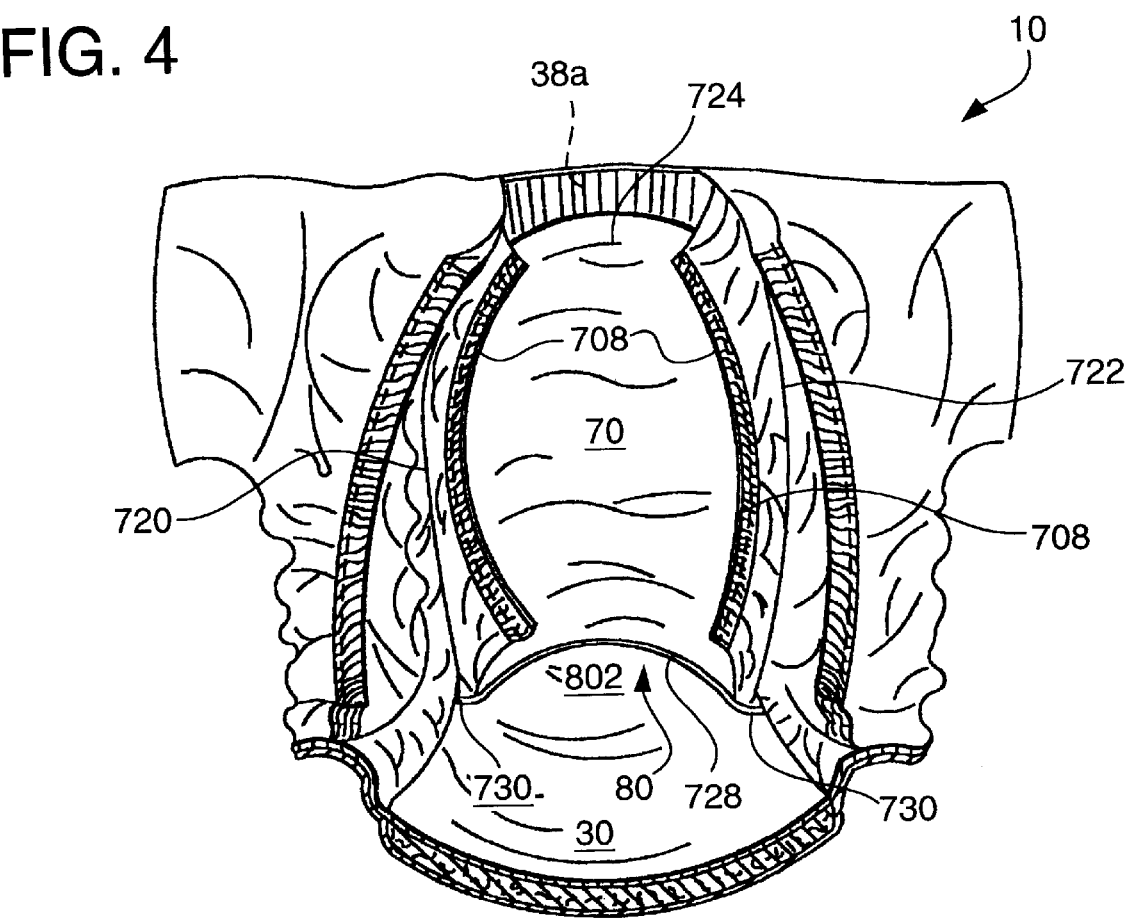
FIG. 4 is a sectional view taken along line 4—4 in FIG. 3 illustrating the pocket containment structure of the preferred embodiments.
Figure 5:
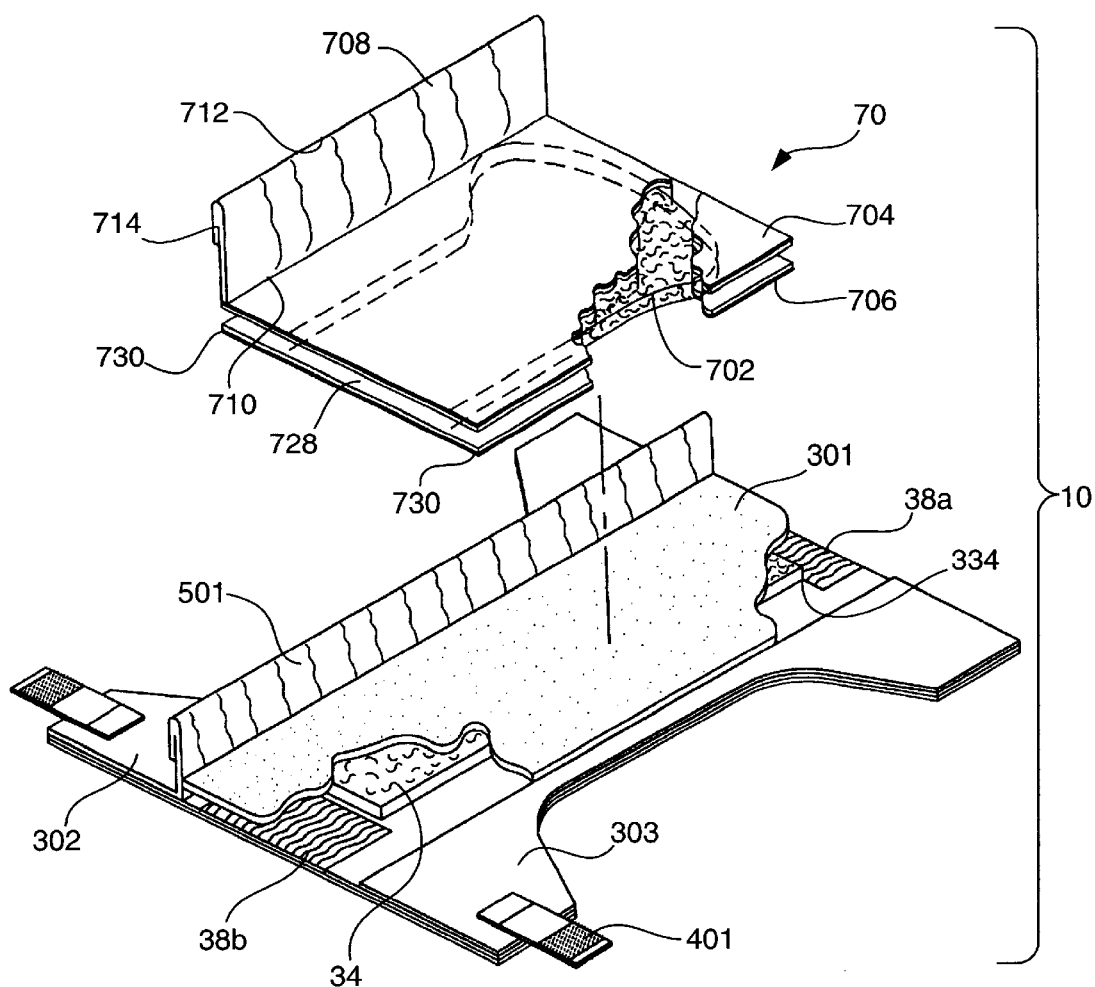
FIG. 5 is an exploded, partial cut away perspective view of the absorbent garment illustrating the upper core elevated above the lower core with the effects of the elastics removed and with the right leg gathers omitted for clarity.

As shown in FIGS. 3–5, in addition to FIGS. 1–2, the absorbent article 10 of the preferred embodiments further includes an upper absorbent structure 70 comprising, in a first preferred embodiment, a conventional fluff pulp absorbent core 702 with or without SAP (or some other equivalent absorbent material) disposed between an upper topsheet 704 and a backing layer or layers 706, such as synthetic nonwoven or tissue layer. The upper absorbent structure 70, illustrated for example in FIGS. 1 and 5, is generally rectangular when the forces of the elastics are removed. The upper absorbent core 702 may be either rectangular or T-shaped (as depicted in FIG. 5).

A second pair of inboard leg gathers 708 are preferably disposed along and attached to lateral side edges of the upper absorbent structure 70. Leg gathers 708 are disposed inboard of the outer pair of leg gathers 501, 502 and likewise are positioned on opposite sides of a longitudinal center line 60 of the absorbent article. As with the outer pair of leg gathers 501, 502, the inner pair of leg gathers 708 include a proximal end 710 and a distal end 712 (FIG. 2). The distal end 712 of the inboard leg gathers 708 includes a portion 714 which is folded over onto itself defining a pocket 716 in which one and preferably at least two elasticized threads 718 are disposed. The pair of inboard standing leg gathers 708 are preferably hydrophobic. The proximal end 710 of the inner pair of standing leg gathers 708 preferably extends around and under the lateral side edges 720 of the upper absorbent structure 70 and, in combination with the backing layer 706, substantially encase the fluff pulp or equivalent absorbent material 702 within the upper absorbent structure 70.

The upper absorbent structure 70 is preferably attached along three edges 720, 722, 724 to the lower topsheet 30. First, the parallel lateral side edges 720, 722 of the upper absorbent structure 70 are preferably adhesively attached to lower topsheet 30 or other subjacent components of the absorbent garment along lines of attachment 726 (FIG. 2) corresponding substantially to the lateral side edges 342, 343 of the lower core 34. After attachment to the lower topsheet 30, the upper absorbent structure 70 is preferably positioned substantially completely between the outer pair of standing leg gathers 501, 502. At its rear edge 728, the upper absorbent structure 70 is attached only at the corners 730 to topsheet 30 or other subjacent components of the absorbent garment. The front edge 724 of the upper absorbent structure 70 is attached to the absorbent garment near the front waist elastic 38a.

With particular reference to FIGS. 3 and 4, an arch-shaped pocket opening 80 is formed between the corners 730 of the rear edge 728 of the upper absorbent structure 70. The elastication of the inboard pair of leg gathers 708 tends to cause the unattached rear edge 728 of the upper absorbent structure 70 to rise above the surface of the lower topsheet 30. The containment pocket 802 thus formed is ideally suited to accept forwardly moving BM and contain the same beneath the upper absorbent structure 70. The upper absorbent structure 70, on the other hand, is designed to acquire and retain urine deposits. Since the urine tends to be retained within the upper absorbent core 702, while BM is retained within the containment pocket 802 formed between the upper and lower absorbent cores 34, 702, urine and BM are substantially isolated from one another.

In use, the arched pocket opening 80 may be collapsed when the wearer of the absorbent garment is seated. Even in this situation, the upper absorbent structure 70 tends to prevent the forward migration of BM. When the arched pocket opening 80 is collapsed, the rear edge 728 of the upper absorbent structure 70 forms a dam-like barrier against the forward migration of BM. The dam-like barrier is formed from the nominal thickness of the upper absorbent core 702, backing layer and topsheet. After the pressure is removed, for example, if the wearer of the absorbent garment stands, the rear edge 728 of the upper absorbent structure 70 once again tends to assume an arch-like profile allowing any fluid BM resting against the dam-like barrier of the rear edge 728 to migrate into the waste containment pocket 802.

The pocket opening 80 formed between the unattached rear edge 728 of the upper absorbent structure 70 and the lower topsheet 30 is intended to encompass configurations whereby the pocket opening 80 lies flat against lower topsheet 30 or other subjacent components and configurations whereby the pocket opening 80 rises above the lower topsheet 30 or other subjacent components.

The upper absorbent core 702 in the first preferred embodiment is preferably made from a combination of fibrous and super absorbent polymer (SAP) gelling additives. For example, the upper absorbent core 702 may comprise cellulose fluff pulp, cellulose acetate fibers, rayon fibers, cotton fibers, or any other equivalent fibrous absorbent material that may be impregnated with SAP particles. The upper absorbent core 702 preferably is formed from a combination of SAP and fibrous additives resulting in basis weights of 500–1100 grams per square meter, and more preferably of basis weights of 700–900 grams per square meter at a SAP concentration of about 20%–50%, preferably about 35% SAP concentration.

Alternatively, either of the upper or lower absorbent cores 702, 34 of the preferred embodiments may be formed from a composite fiber laminate structure as is more fully disclosed in commonly assigned U.S. patent application Ser. No. 09/050,003, and which is hereby incorporated by reference. Any other known absorbent material in the art may be employed in connection with the preferred embodiments. For example, pulpless and other equivalent absorbent cores are intended to be included within the scope of the invention. In any event, due to the wide variety of absorbent materials, construction and systems currently available, the invention is not intended to be limited to any specific materials, constructions or systems of absorbent core components.

More specifically, with regard to alternative configurations for the absorbent material contained within the upper and lower absorbent cores 702, 34, the upper absorbent core 702 may, rather than being formed from fiber/SAP, comprise a thinner absorbent material such as airlaid fluff pulp roll good (with or without SAP). In this alternative embodiment, the upper absorbent structure 70 has substantially the same construction and lines or zones of attachment to the lower topsheet 30 as in the embodiment described previously, but rather than fiber/SAP, the upper absorbent core 702 comprises a thinner material, such as an airlaid fluff pulp roll good. In this case, the lower absorbent core 34 is preferably formed from the fibrous/SAP components described previously.

Figure 6:
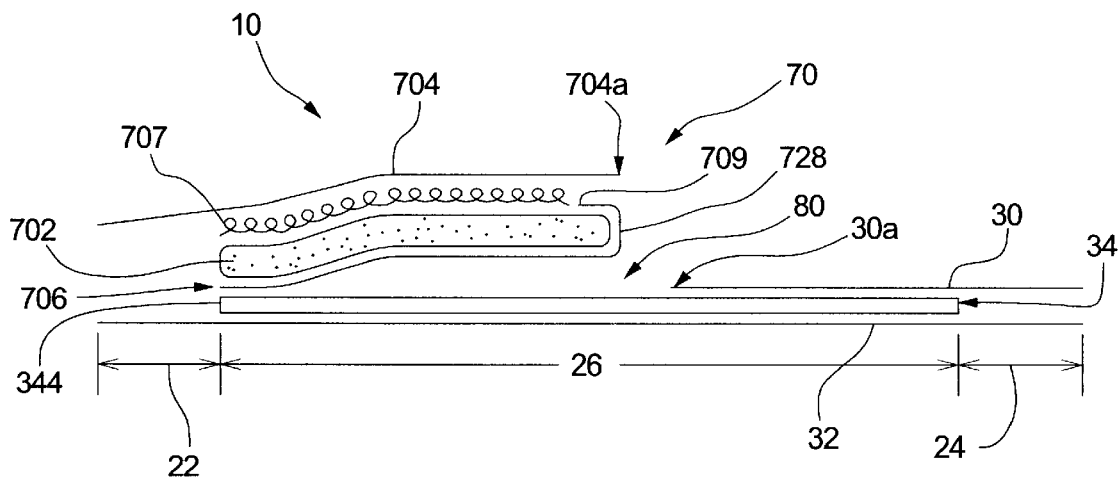
FIG. 6 is a sectional schematic view of the absorbent garment according to the first preferred embodiment taken along line 6—6 in FIG. 1.

With reference to FIG. 6, there is illustrated a cross-sectional schematic diagram of the diaper according to one preferred embodiment. As seen in FIG. 6, the absorbent garment 10 includes a lower topsheet 30 and a backsheet 32, between which is at least partially sandwiched the lower absorbent core 34. The lower absorbent core 34 in the first preferred embodiment, as stated earlier, preferably comprises an airlaid fluff pulp roll good layer which may optionally be impregnated with super absorbent gelling particles. The lower topsheet 30 in the embodiment illustrated preferably extends from about the rear waist portion 24 to an area in the crotch region 26 subjacent the arch-shaped pocket opening 80.

The absorbent garment further includes an upper absorbent structure 70 comprising conventional fluff pulp or equivalent absorbent material 702 disposed between an upper topsheet 704 and a backing layer 706. The end 709 of the backing layer 706 above the pocket opening 80 preferably wraps around the end of the fluff pulp layer (which may optionally contain super absorbent gelling particles) to encase and retain the structural integrity of the upper fluff core 702. Alternatively, the upper topsheet 704 may wrap around end edge 728 beneath backing sheet 706. A transfer layer 707 may optionally be disposed between the upper topsheet 704 and the fluff pulp layer 702.

In the preferred embodiment of FIG. 6, the upper topsheet 704 and lower topsheet 30 may be derived from the same cover stock material. That is to say, the rear edge 704a of upper topsheet and the front edge 30a of lower topsheet may have been, at one point in the manufacturing process, joined such that the upper topsheet 704 and lower topsheet 30 formed a continuous roll good material. Then, during manufacture, the unitary roll material may be severed at edges 704a, 30a to separate the upper topsheet 704 from the lower topsheet 30.

It will be readily recognized by those of ordinary skill in the art that the upper absorbent core 702 and the lower absorbent 34 may be of the same (FIG. 2) or different thicknesses, depending on the material chosen for the respective absorbent cores. In the example of the first preferred embodiment, it will be readily appreciated that the upper absorbent core 702, formed from conventional fluff-pulp with optional SAP impregnation, will be relatively thicker than the lower absorbent core 34 formed of an airlaid fluff pulp roll good layer. In any event, the relative dimensions of the absorbent cores 34, 702 in FIG. 2 is for illustrative purposes only and is not intended to limit the scope of the invention. In fact, in alternative embodiments, the absorbent cores are reversed such that the upper absorbent core 702 is formed from an airlaid fluff pulp layer and the lower absorbent core 34 is fluff-pulp. Consequently, in these alternative embodiments, the upper absorbent core 702 is relatively thinner than the lower absorbent core 34. In the alternative embodiments, as in the first preferred embodiment, mixing of BM and urine is substantially reduced, and even if mixing occurs, the mixture tends to be prevented from coming into contact with the skin and the genital area.

Figure 7:
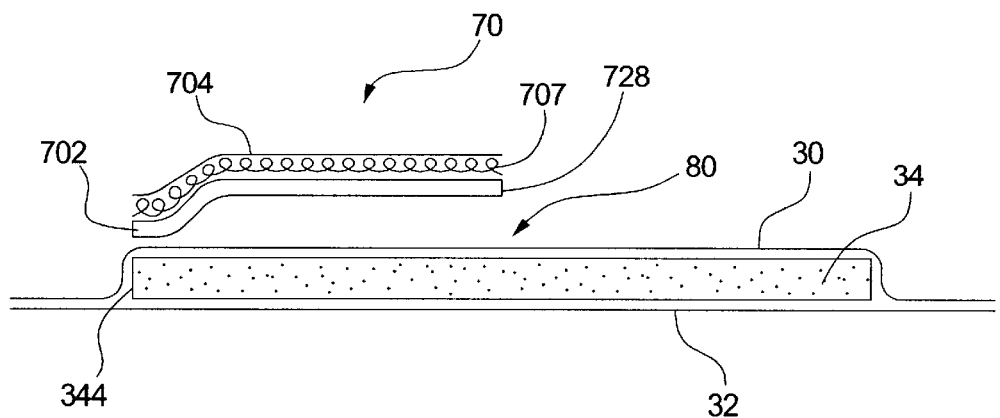
FIG. 7 is a schematic sectional view similar to FIG. 6 showing the absorbent garment according to another preferred embodiment.

One such further alternative embodiment is illustrated in FIG. 7. There, the materials comprising the absorbent components of the upper and lower absorbent cores 702, 34 are reversed. Specifically, the upper absorbent core 702 comprises an airlaid fluff pulp layer covered by an upper topsheet layer 704. Since by virtue of the nature of airlaid fluff pulp the individual fibers are firmly held in place due to adhesive additives, the necessity of a backing layer 706 containing and confining the fibers of the upper absorbent core 702 may be dispensed with. If preferred, transfer and other acquisition layers 707 may be layered on top of the airlaid fluff pulp layer 702 beneath the upper topsheet 704. The airlaid fluff pulp layer 702 may also be impregnated with SAP particles for enhanced urine containment.

The lower absorbent core material 34 of this alternative embodiment may comprise cellulose fluff pulp or other equivalent fibrous materials, and in this case would generally be thicker than the upper absorbent core 702. The lower absorbent core 34 of the alternative embodiment may be impregnated with SAP particles, or may comprise a laminate structure as described in copending U.S. patent application Ser. No. 09/050,003.

Notwithstanding the material employed as the absorbent component in the upper 702 and lower 34 absorbent cores, the basic structure of the absorbent garment remains the same. That is, the end or rear edge 728 of the upper absorbent structure 70 preferably remains substantially unattached to the lower topsheet 30 or other subjacent components of the absorbent garment, and is elasticized at its lateral sides by an inboard pair of standing leg gathers 708, tending to cause the end edge 728 of the upper absorbent core to form a pocket opening 80 and imparting a curvature to the upper absorbent structure 70. The upper absorbent structure 70 is preferably sized so that urine insults are generally directed upon, collected and retained within the upper absorbent structure 70 and BM deposits are directed upon the lower topsheet 30 and transferred into the opening 80 of containment pocket 802 so that the genitals are not soiled by BM.

As a further alternative embodiment, the lower absorbent core 34, in either of the embodiments of FIGS. 6 and 7, may be configured having a front edge 344 which extends to and terminates in the crotch area 26 substantially subjacent the rear edge 728 of the upper absorbent structure 70. Such a construction would, of course, result in material savings in that the lower absorbent core 34 would not extend the entire length of the absorbent garment. In this case, the BM would be contained within the containment pocket 802 between the backsheet 32 or a tissue layer overlying the backsheet 32 and the underside of the upper absorbent structure 70. Since BM generally is not for the most part absorbed by an absorbent core, but rather remains on the surface of the topsheet, the fact that the containment pocket 802 in an alternative embodiment does not itself have a separate absorbent core therebeneath will not diminish the effectiveness of the absorbent garment. In fact, once the BM has migrated into the containment pocket 802, the objectives of keeping BM from soiling the genitals and isolating the urine from the BM have been achieved.

Without intending to limit the preferred embodiments, the degree to which the upper absorbent structure 70 extends through the crotch area 26 is an important factor in the success of keeping BM from soiling the genitals and isolating urine and BM. In fact, if the upper absorbent structure 70 is too short such that the rear edge 728 only begins to enter the crotch area 26, it will not adequately protect the genital area from soiling. On the other hand, if the upper absorbent structure 70 is too long such that the rear edge 728 extends substantially through the crotch area 26, the BM may in the first instance impinge upon the upper topsheet 704 and migrate forward to soil the genitals. Consequently, proper positioning of the opening of the containment pocket relative to the anus and genitals of the wearer is an important consideration in the overall success of the design of the garment.

At the very least, in each of the preferred embodiments, the rear edge 728 of the upper absorbent structure 70 should extend into but not through the crotch area 26 of the absorbent garment. In its most preferred form, the absorbent garment of the preferred embodiments positions the rear edge 728 of the upper absorbent structure between the genitals and the anus of the wearer. The center line of the diaper is designed to correspond generally with the lowest point of the crotch (when the wearer is in a standing position) or center line of the wearer. The rear edge 728 of the upper absorbent structure 70 should preferably be positioned slightly in front of the point of lowest curvature of the absorbent garment when worn by the wearer. Some absorbent garments are designed with extended waist openings. Even in these garments, the point of lowest curvature may be readily ascertained, and from there, the rear edge 728 of the upper absorbent structure 70 may be positioned slightly ahead of the point of lowest curvature.

In order to position the rear edge 728 of the upper absorbent structure 70 between the genitals and the anus of the wearer, the rear edge 728 should preferably be positioned about 5–40 mm in front of the center line of the diaper, ie., the lowest point of the crotch or the lowest point of curvature, more preferably about 10–30 mm in front of the lowest point of the crotch. and most preferably about 10–20 mm in front of the lowest point of the crotch or center line of the diaper. The optimal distance between the rear edge of the upper absorbent structure and the center line of the diaper tends to lie at the lower end of the range stated for diapers for smaller infants. More specifically, for a size large diaper (for 22–37 lb. infants) of about 488 mm as measured from the front waist edge to the rear edge, where the front edge of the upper absorbent structure is positioned 25 mm from the front waist edge of the diaper, the upper absorbent structure 70 should preferably be about 140–210 mm, and more preferably about 180–200 mm and most preferably about 195 mm in length as measured from the front end to the rear end of the upper structure 70. When the upper absorbent structure 70 is about 195 mm in length as measured from the front edge 724 to the rear edge 728 thereof, it has been found that BM generally contacts the lower topsheet 30, urine generally contacts the upper topsheet 704, and soft BM generally migrates in the direction of and into the containment pocket 802, thereby isolating the urine and BM and preventing the soiling of genitals.

Figure 8:
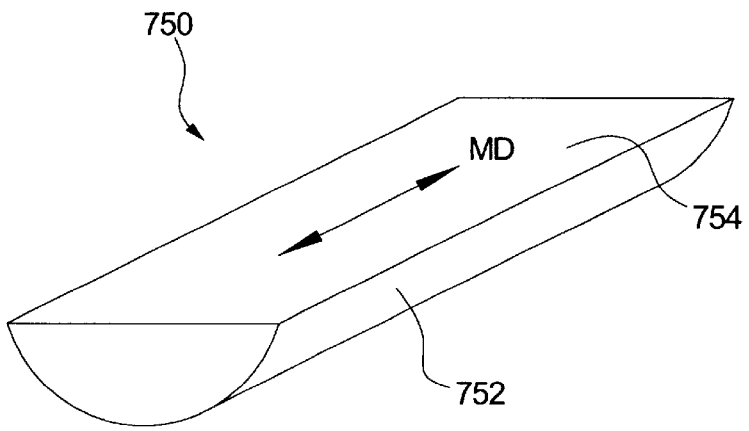
FIG. 8 is a schematic view of a template employed to impart curvature to the lower absorbent core.
Figure 9:
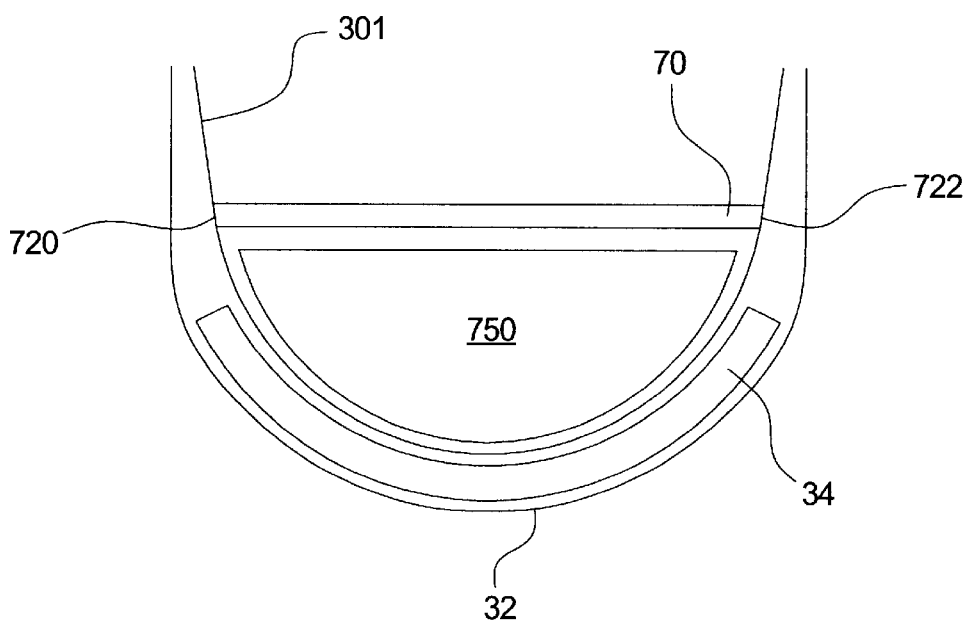
FIG. 9 is a schematic view of the template of FIG. 8 showing the lower absorbent core wrapped therearound and the upper absorbent core attached to the lower absorbent core while curvature is applied thereto.

In each of the foregoing preferred embodiments, a curvature is preferably applied to the lower absorbent core 34 before the upper absorbent structure 70 is attached to the lower topsheet panel 301. The curvature can be applied using a semi-cylindrical template around which the lower absorbent core 34 is wrapped during manufacture. For example, as shown schematically in FIGS. 8–9, the template 750 may include a curved lower section 752 and a flat top section 754. The lower absorbent core 34 is wrapped around the curved lower portion 752 of the template 750 as the garment is being manufactured in the machine direction (MD). The upper absorbent structure 70 is then attached along its edges 720, 722 to the lower topsheet panel 301 and the template is removed.

It has been discovered that it is more effective to apply the curvature to the lower absorbent structure than to the upper absorbent structure 70. However, it is possible and within the scope of the preferred embodiments to use a template similar to that of FIG. 8, but reversed so that the curvature faces upwards. In this case, the upper absorbent structure 70 is wrapped therearound. It has also been discovered that once the lower absorbent core 34 has been curved around template 750 such that an arch-shaped pocket opening 80 is formed between the end 728 of the upper absorbent structure 70, the inner pair of leg gathers 708 attached to the upper absorbent structure 70 may be removed altogether.

In its most preferred form, the template 750 may be formed with a taper such that it has a smaller radius of curvature in the portion corresponding to the crotch opening than in the portion corresponding to the waist opening. The radius of curvature of the template in the portion corresponding to the waist opening should be larger than the radius of curvature of the wearer's waist to ensure proper fit of the diaper around the waist.

The deviation between the radius of curvature along the length of template 750 should be minimal, otherwise, as the absorbent garment travels in machine direction across template 750, the side and end edges 720, 722, 724 (FIG. 1) of upper absorbent structure 70 may become detached from the subjacent components of the absorbent garment. Consequently, to prevent such detachment, the template may be eliminated altogether and the upper absorbent structure 70 attached directly to the subjacent component. Still further yet, rather than employing template 750, the curvature may be imparted to the lower absorbent structure by employing a template depression on a vacuum drum.

Figure 10:
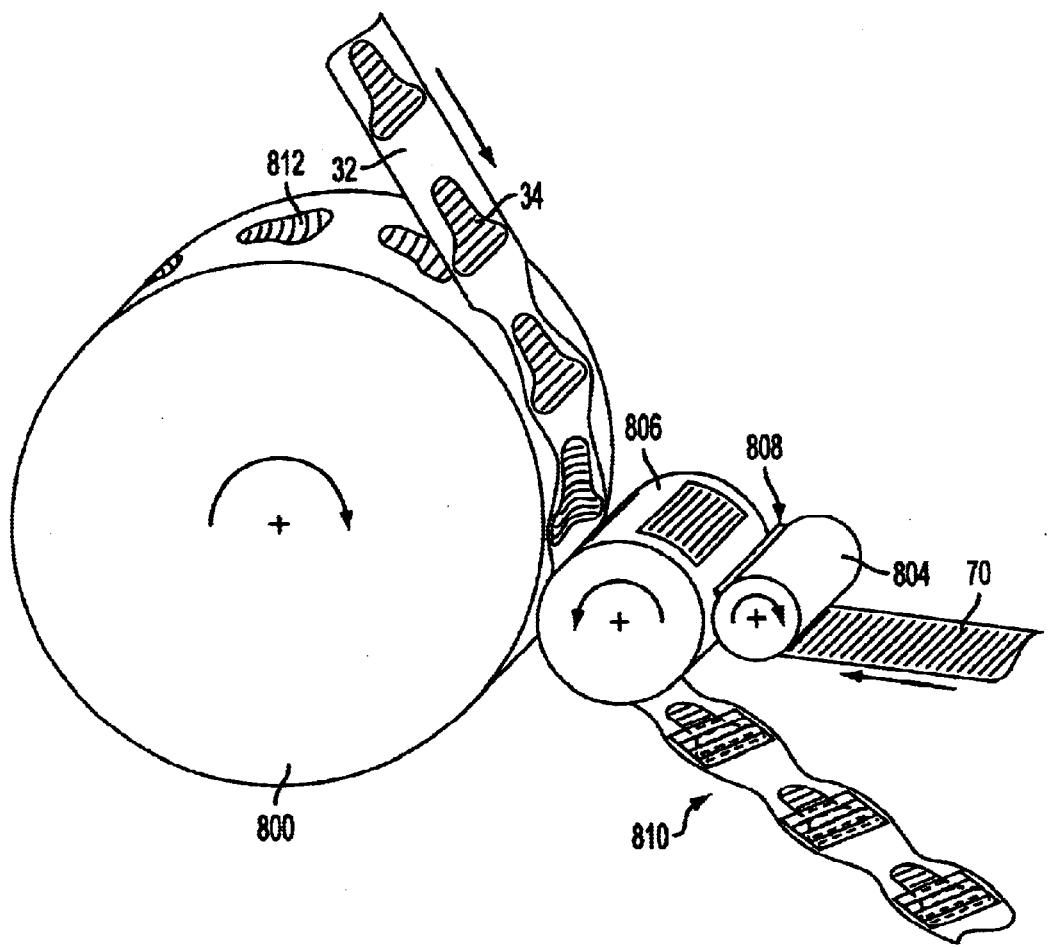
FIG. 10 depicts a schematic illustration of an alternative manufacturing process for imparting curvature to the lower absorbent core to create the pocket opening in the absorbent garment.

For example, as schematically depicted in FIG. 10, vacuum drum 800 is formed with a plurality of template depressions 812 formed therearound. The backsheet 32 has lower absorbent core 34 laid thereon and is then wound around vacuum drum 800. Template depression 812, in conjunction with vacuum drum 800, imparts a curvature to the lower absorbent structure. The upper absorbent structure 70 is wound between drums 804 and 806. Drum 804 includes a knife edge 808 which severs the upper absorbent structure 70 into individual components for application above respective template depressions 812. The combined upper absorbent structure and lower absorbent structure at point 810 may then have inboard leg gathers and other functional components added thereto.

The invention has been described in connection with the use of a BM pocket in a diaper. It should be understood, however, that the basic concept of the invention is amenable to different absorbent garment constructions. For instance, the BM pocket may be incorporated into adult absorbent incontinent products as well as training pants and fem-care pads. The claims are intended to cover all of the various types of disposable absorbent products, including diapers, training pants and adult incontinence products.

While the preferred embodiments have been described in connection with imparting a curvature to either the upper or lower absorbent structures, the curvature, though preferred, may be omitted from the absorbent garment and the garment will still generally prevent the forward migration of BM. Even without the curvature, the preferred embodiments will generally prevent BM from soiling the genitals and isolate the urine from BM to reduce the incidence of diaper rash.

The invention has been described in connection with the preferred embodiments. These embodiments, however, are merely for example only and the invention is not restricted thereto. It will be understood by those skilled in the art that other variations, modifications and equivalent absorbent garment structures can easily be made within the scope of the invention as defined by the appended claims.

We claim:

1. An absorbent garment for isolating urine from BM and adapted to prevent genitals of an intended wearer of the garment from being soiled by BM, comprising:
   a front waist region, a rear waist region and a crotch region defined between said front and rear waist regions;
   leg openings defined between said front and rear waist regions on opposite sides of said crotch region;
   a backsheet;
   a lower absorbent structure extending from said rear waist region at least into said crotch region, said lower absorbent structure comprising:
   a lower topsheet; and
   a lower absorbent core positioned between said lower topsheet and said backsheet; and
   an upper, partial length absorbent structure extending from said front waist region into said crotch region, said upper, partial length absorbent structure comprising:
   an upper topsheet; and
   an upper absorbent core positioned beneath said upper topsheet;
   said upper absorbent structure defined by a front edge disposed in said front waist region, a rear edge disposed in said crotch region and a pair of side edges extending from said front edge to said rear edge;
   a first pair of standing leg gathers respectively attached to said upper absorbent structure along the side edges thereof;
   a second pair of standing leg gathers associated with said lower topsheet and extending from said front waist region, through the crotch region, and into said rear waist region along opposite sides of a longitudinal centerline of the absorbent garment, said first pair of standing leg gathers disposed inboard of said second pair of standing leg gathers;
   wherein at least one of the lower topsheet and the lower absorbent core extends substantially entirely from said rear waist region to said front waist region; and
   wherein said front edge and said side edges of said partial length absorbent structure are directly attached to said lower absorbent structure and said rear edge of said partial length upper absorbent structure is substantially directly unattached to said lower absorbent structure.

2. The absorbent garment of claim 1, wherein a pocket opening is formed between said unattached rear edge of said upper absorbent structure and said lower absorbent structure to thereby form a containment pocket beneath said upper absorbent structure.

3. The absorbent garment of claim 1, further comprising leg elastic positioned adjacent respective said leg openings and extending at least through the crotch region.

4. The absorbent garment of claim 1, wherein said upper absorbent core is selected form the group consisting essentially of fluff pulp roll good, fluff pulp roll good containing SAP, conventional fluff pulp and conventional fluff pulp containing SAP.

5. The absorbent garment of claim 1, wherein said lower absorbent core is selected from the group consisting essentially of fluff pulp roll good, fluff pulp roll good containing SAP, conventional fluff pulp and conventional fluff pulp containing SAP.

6. The absorbent garment of claim 1, wherein said lower topsheet extends substantially entirely from said rear waist region to said front waist region.

7. The absorbent garment of claim 1, wherein a pocket opening is formed between said unattached rear edge of said upper absorbent structure and said lower absorbent structure to thereby form a containment pocket beneath said upper absorbent structure, said lower absorbent structure extending from said rear wais region to a position in said crotch region substantially subjacent said pocket opening.

8. The absorbent garment of claim 1, wherein said lower absorbent core extends substantially entirely from said rear waist region to said front waist region.

9. The absorbent garment of claim 1, wherein said upper absorbent structure further comprises a backing layer, said upper absorbent core positioned between said upper topsheet and said backing layer.

10. The absorbent garment of claim 1, wherein said absorbent garment has a point of lower curvature when worn, and said upper absorbent structure is sized so that said rear edge is positioned slightly ahead of said point of lowest curvation in the direction of said front waist region.

11. The absorbent garment of claim 10, wherein said point of lowest curvature substantially corresponds to a point spaced equally between the front and rear waist regions.

12. The absorbent garment of claim 10, wherein said upper absorbent structure is sized so that said rear edge is positioned about 5–40 mm ahead of said point of lowest curvature.

13. The absorbent garment of claim 1, wherein said upper absorbent structure is sized so that said rear edge is positionable substantially between the genitals and an anus of the intended wearer.

14. An absorbent article comprising:
   a front waist region, a rear waist region, a crotch region between said front and rear waist regions;
   leg openings defined between said front and rear waist regions on opposite sides of said crotch region;
   a backsheet;
   an upper absorbent structure comprising an upper topsheet and an upper absorbent core positioned beneath said upper topsheet, said upper absorbent structure defined by a rear edge, a front edge, and a pair of side edges extending from said front edge to said rear edge; said front edge of said upper absorbent structure extending near and attaching to the absorbent article in said front waist region, said rear edge of said upper absorbent structure extending into and terminating at a longitudinal position of the absorbent article corresponding substantially to said crotch region, said side edges attaching to the absorbent article along their length, said rear edge of said upper absorbent structure substantially free from direct attachment to the absorbent article except at the corners thereof;

a containment pocket formed beneath said upper absorbent structure, said containment pocket including a pocket opening defined beneath said rear edge of said upper absorbent structure, said pocket opening adapted to allow for the collection of solid waste for storage beneath said upper absorbent structure;

a lower absorbent structure including a lower topsheet and a lower absorbent core positioned between said backsheet and said lower topsheet;

a first pair of standing leg gathers associated with said lower topsheet, said first pair of leg gathers positioned on opposite sides of a longitudinal centerline of the absorbent article through at least a portion of said crotch region; and a second pair of standing leg gathers attached to said upper absorbent structure and disposed on said oppositie sides of said longitudinal centerline inboard of said first standing leg gathers;

each of said standing leg gathers having proximal edges and distal edges, said proximal edges of said first pair of standing leg gathers attached adjacent respective side edges of said lower absorbent structure and said proximal edges of said second pair of standing leg gathers attached adjacent respective said side edges of said upper absorbent structure.

15. The absorbent garment of claim 14, wherein said distal edges of said second pair of standing leg gathers are elasticized, to thereby cause the pocket opening to assume an arched profile.

16. The absorbent article of claim 14, wherein said second pair of standing leg gathers extend from said front edge to said rear edge of said upper absorbent structure.

17. The absorbent article of claim 14, wherein said front edge of said lower absorbent structure extends beneath said rear edge of said upper absorbent structure, into said containment pocket and terminates near said front waist region.

18. The absorbent article of claim 14, said upper absorbent core comprising an airlaid pulp roll good having a basis weight of about 30–150 grams per square meter and said lower absorbent core comprising fluff pulp and SAP.

19. The absorbent article of claim 18, said airlaid pulp roll good containing about 10–60% by weight SAP.

20. The absorbent article of claim 14, wherein said upper absorbent core comprises fluff pulp and SAP and said lower absorbent core comprises an airlaid fluff pulp roll good.

21. The absorbent article of claim 14, wherein said upper absorbent core comprises fluff pulp and SAP, and said upper absorbent structure further comprises a backing layer enclosing a lower of said upper absorbent core so that said fluff pulp is sandwich between said topsheet and said backing layer.

* * * * *